United States Patent
Jung et al.

(10) Patent No.: US 11,541,147 B2
(45) Date of Patent: Jan. 3, 2023

(54) HYALURONIC ACID COMPOSITION AND PREPARATION METHOD THEREFOR

(71) Applicant: CG BIO CO., LTD., Gyeonggi-do (KR)

(72) Inventors: Su Hyun Jung, Gyeonggi-do (KR); Jun Hyuk Seo, Gyeonggi-do (KR); Hyun Seung Ryu, Gyeonggi-do (KR); Hak Su Jang, Gyeonggi-do (KR)

(73) Assignee: CG BIO CO., LTD., Gyeonggi-do (KR)

( * ) Notice: Subject to any disclaimer, the term of this patent is extended or adjusted under 35 U.S.C. 154(b) by 498 days.

(21) Appl. No.: 15/756,706

(22) PCT Filed: Sep. 2, 2015

(86) PCT No.: PCT/KR2015/009229
§ 371 (c)(1),
(2) Date: Mar. 1, 2018

(87) PCT Pub. No.: WO2017/039030
PCT Pub. Date: Mar. 9, 2017

(65) Prior Publication Data
US 2018/0344896 A1    Dec. 6, 2018

(30) Foreign Application Priority Data
Sep. 1, 2015 (KR) .......... 10-2015-0123569

(51) Int. Cl.
*A61L 27/20* (2006.01)
*A61L 27/26* (2006.01)
*A61K 31/728* (2006.01)

(52) U.S. Cl.
CPC .......... *A61L 27/20* (2013.01); *A61K 31/728* (2013.01); *A61L 27/26* (2013.01); *A61L 2400/06* (2013.01); *A61L 2430/34* (2013.01)

(58) Field of Classification Search
CPC .................. A61L 27/20; A61K 31/72
See application file for complete search history.

(56) References Cited

U.S. PATENT DOCUMENTS

| | | | |
|---|---|---|---|
| 5,827,937 A | 10/1998 | Agerup | |
| 8,357,795 B2 | 1/2013 | Lebreton | |
| 2011/0034684 A1* | 2/2011 | Yokokawa | A61K 8/042 536/53 |

FOREIGN PATENT DOCUMENTS

| | | | |
|---|---|---|---|
| JP | 2005-154305 | 6/2005 | |
| KR | 10-2014-0117956 | 10/2014 | |
| KR | 10-2015-0029578 A | 3/2015 | |
| WO | 2012062775 A1 | 5/2012 | |
| WO | 2013/053457 A1 | 4/2013 | |
| WO | WO-2013053457 A1 * | 4/2013 | C08J 3/075 |

OTHER PUBLICATIONS

Examination report No. 2 issued in Australian Application No. 2015407889 dated Aug. 19, 2019.
International Search Report dated Feb. 11, 2016, from International Application No. PCT/KR2015/009229, 4 pages.
Song, Y.S. et al., "Formulation Characteristics of Three Kinds of Elravie(R) Fillers", Korean J Dermatol. Feb. 5, 2014, 2 pages.
Baek, B.S., "DANAE Filler at Daegu Doctor Phil Hospital", Naver Blog, Website address: http://blog.naver.com/doctor_phill/220461266753, Aug. 25, 2015 (English translation).

* cited by examiner

*Primary Examiner* — Shaojia A Jiang
*Assistant Examiner* — Everett White
(74) *Attorney, Agent, or Firm* — Meunier Carlin & Curfman LLC

(57) ABSTRACT

Provided are a hyaluronic acid composition having excellent viscoelasticity and being easily injectable, and a preparation method thereof.

14 Claims, 7 Drawing Sheets

[FIG. 1a]
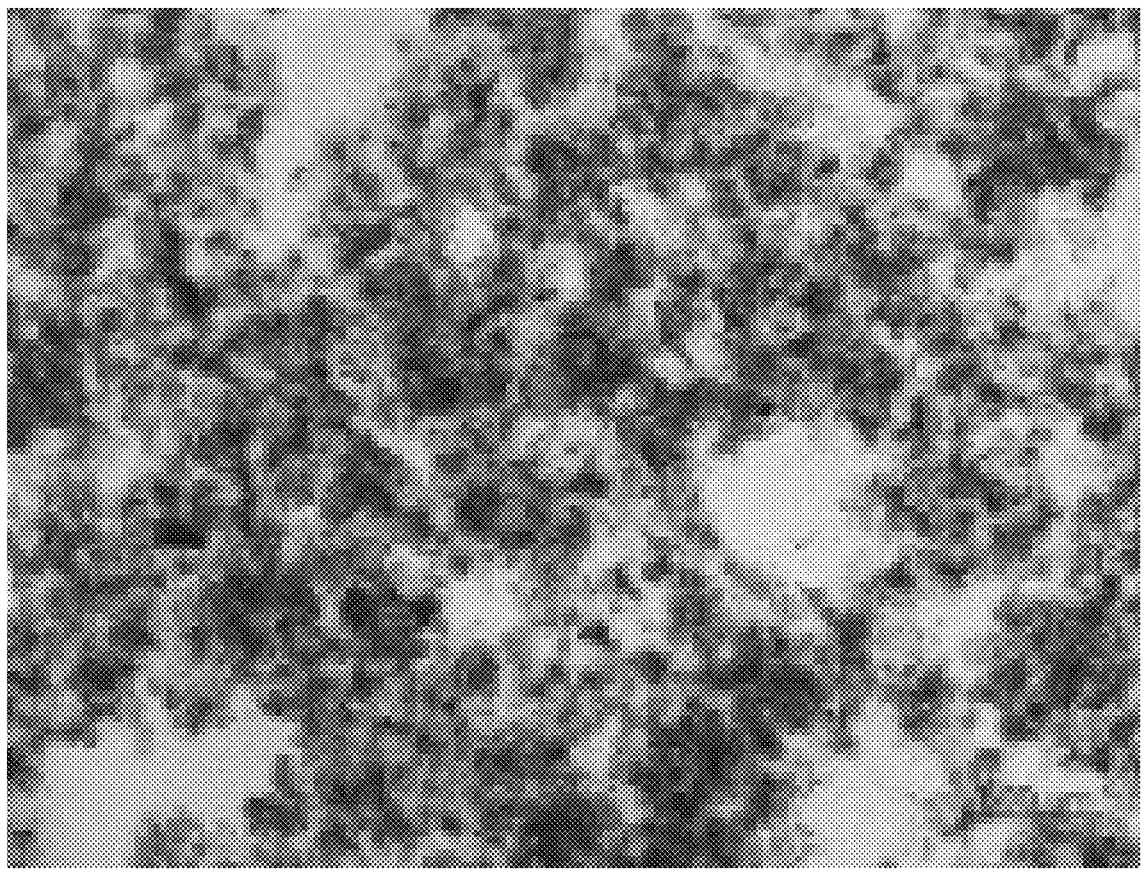

[FIG. 1b]
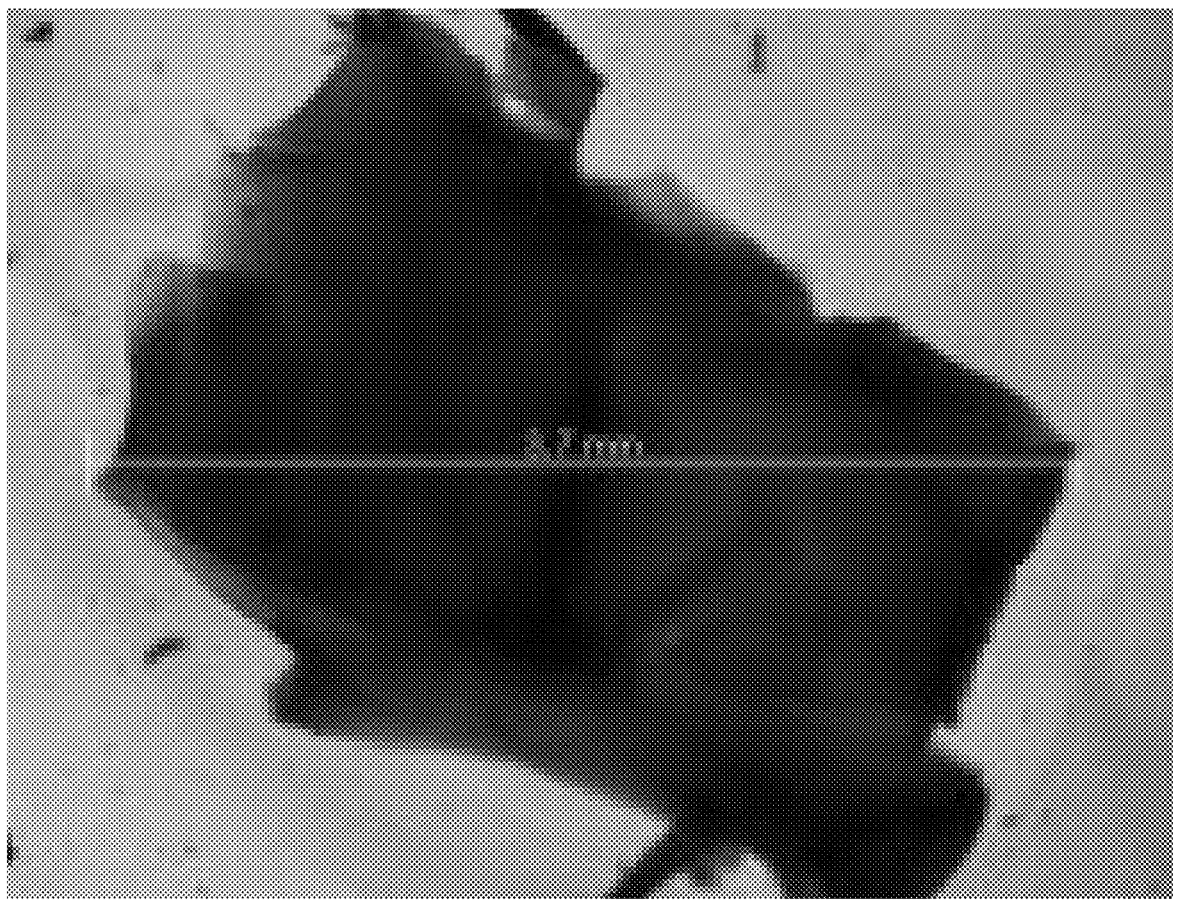

[FIG. 2a]
[FIG. 2b]
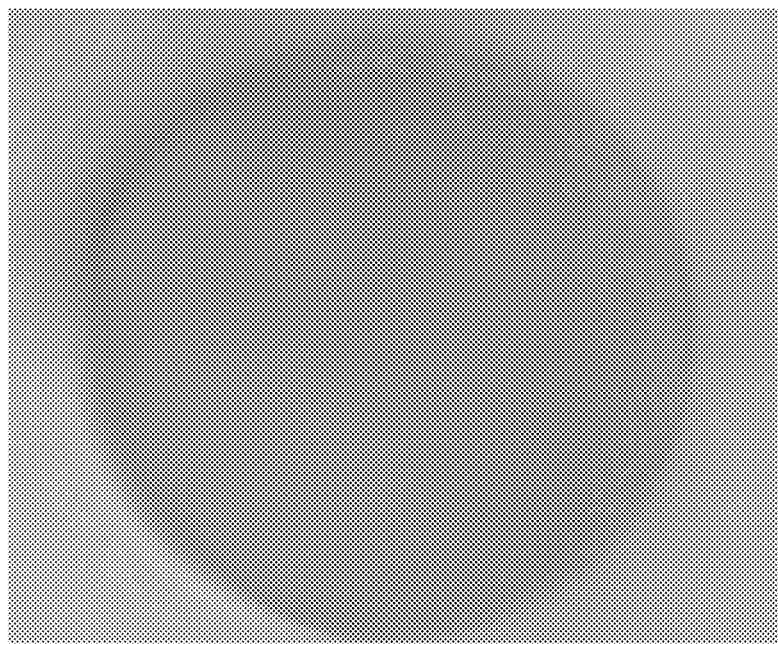

[FIG. 3a]
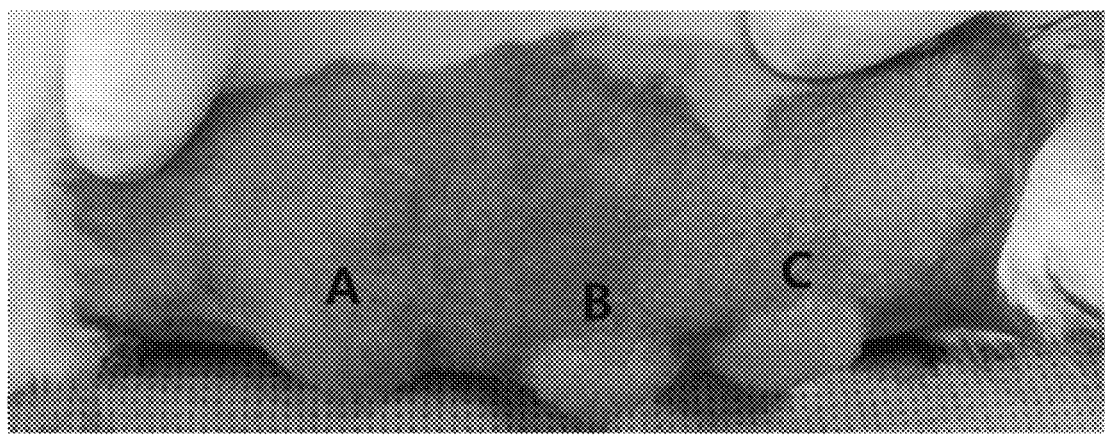
[FIG. 3b]
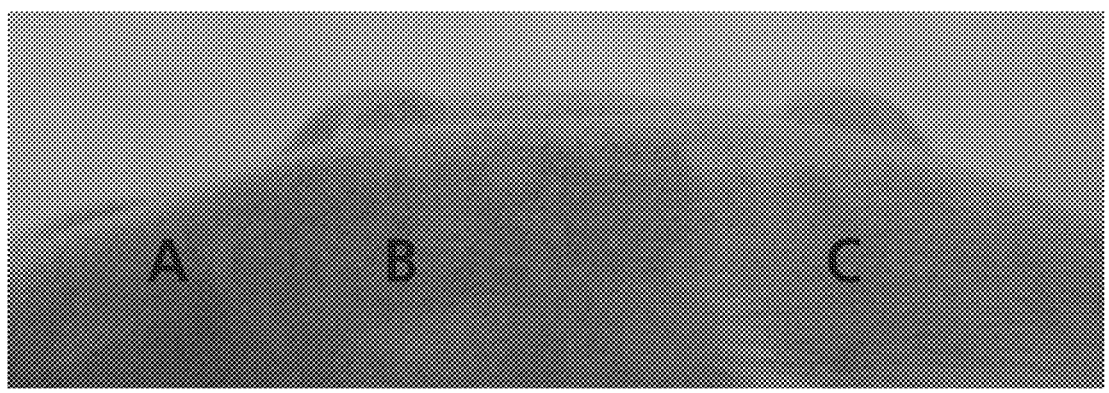

[FIG. 4]
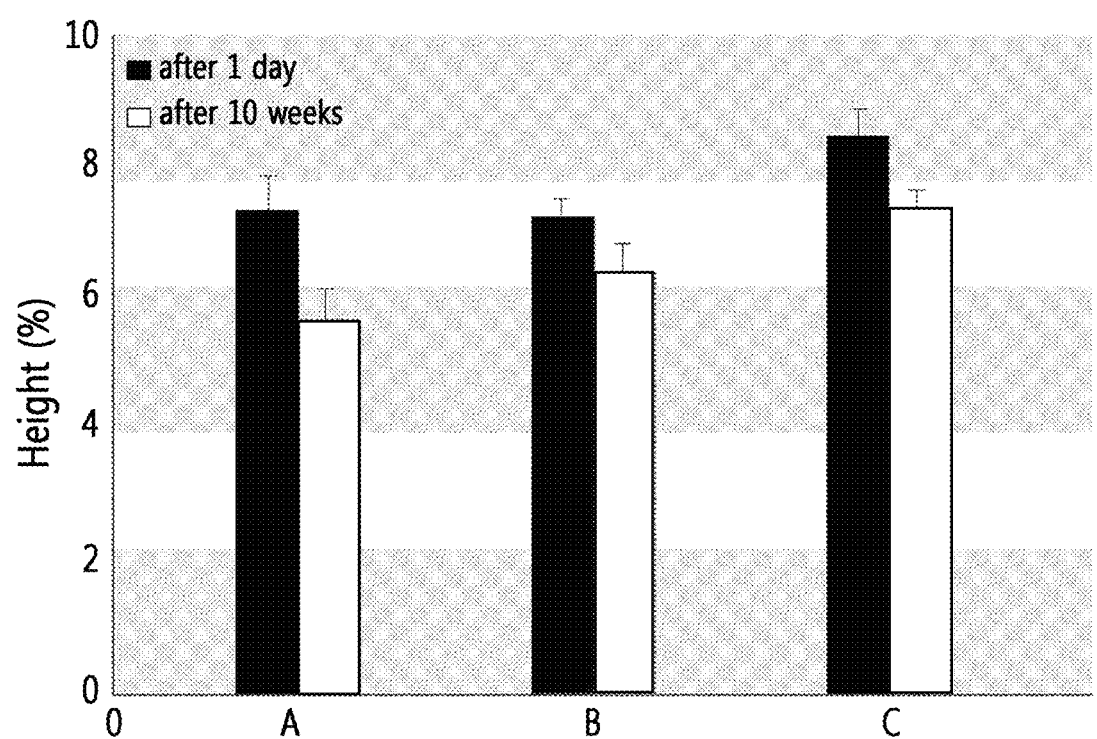

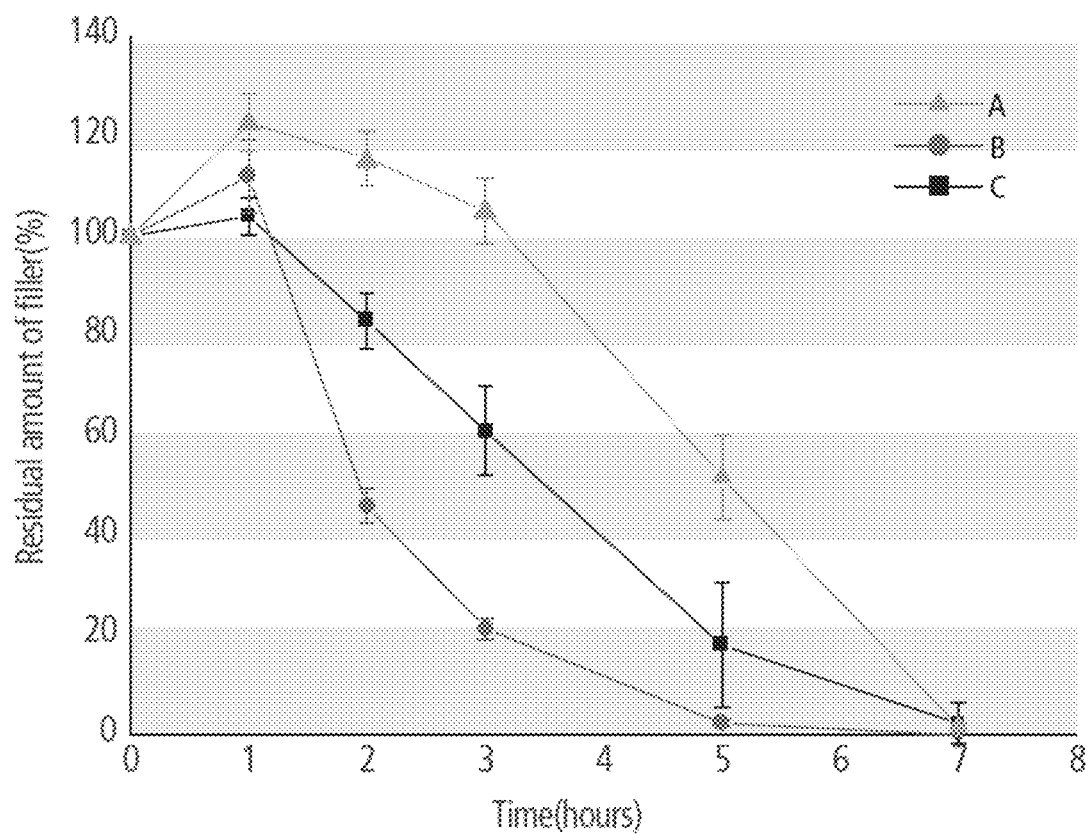
[FIG. 5]

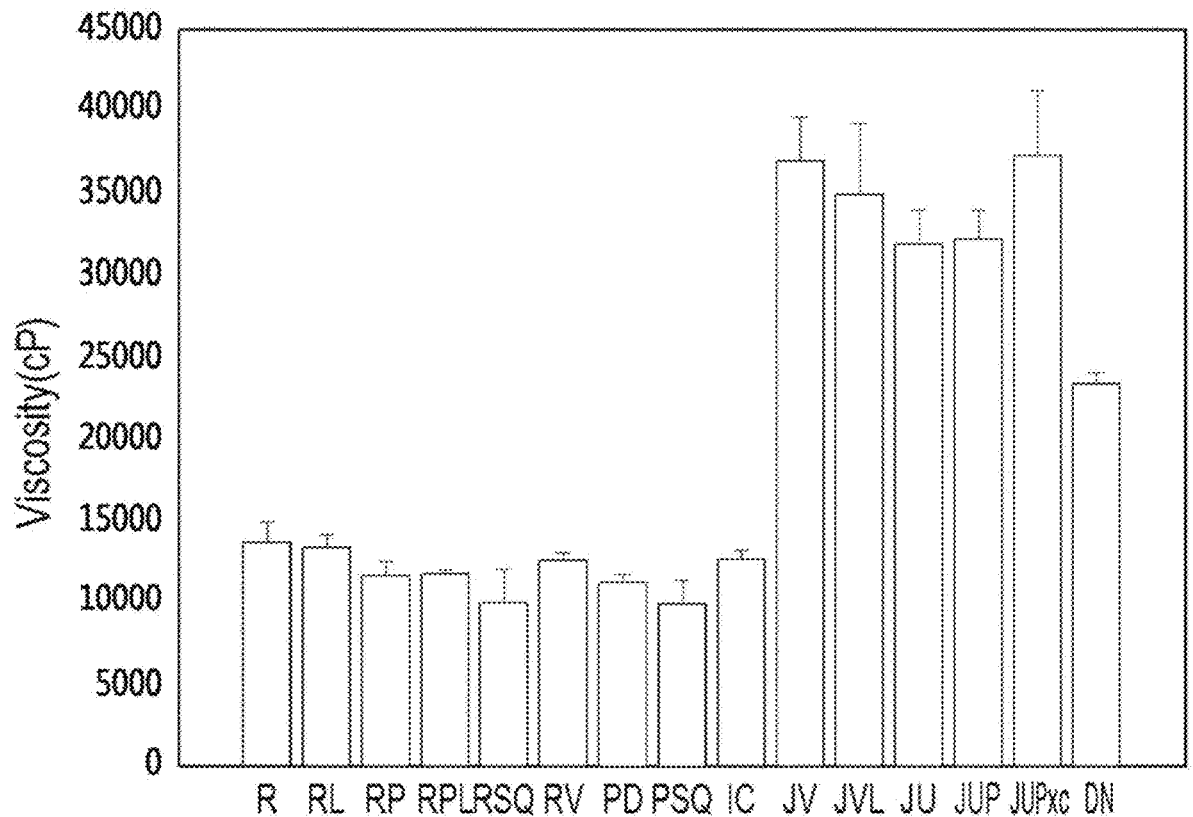
[FIG. 6]
R: Restylane, RL: Restylane lidocaine, RP: Restylane perlane,
RPL: Restylane perlane lidocaine, RSQ: Restylane subq,
RV: Restylane vital, PD: Perfecta deep, PSQ: Perfecta subq,
IC: Yvoire classic, JV: juvederm voluma,
JVL: juvederm voluma lidocaine, JU: juvederm ultra,
JUP: juvederm ultra plus, JUPxc: juvederm ultra plus xc

HYALURONIC ACID COMPOSITION AND PREPARATION METHOD THEREFOR

BACKGROUND OF THE INVENTION

1. Field of the Invention

The present disclosure relates to a hyaluronic acid composition and a preparation method thereof.

2. Description of the Related Art

Hyaluronic acid is a transparent, viscous gel-type product and has high biocompatibility and hydrophilicity. Since 1 molecule of hyaluronic acid attracts 214 water molecules, hyaluronic acid plays an important role in maintaining moisture of the skin and volume and elasticity of the skin. Therefore, dermal fillers containing hyaluronic acid as a component tend to be used to tighten facial skin, improve facial contours and facial wrinkles, and shape facial contours.

However, natural hyaluronic acid has a half-life of only 1 day to 2 days, and therefore, long-term persistence of hyaluronic acid used in fillers is achieved by crosslinking. The crosslinking of hyaluronic acid prevents enzymatic degradation and increases viscosity to give volume to the skin (Yi Seop Song, et al., Korean Journal of Dermatology 2014; 52(2):100-105).

Currently available hyaluronic acid fillers have a monophasic or biphasic nature. Monophasic fillers are entirely composed of homogeneous gel, and thus highly viscous, and are easy to inject and suitable for shaping delicate areas. Biphasic fillers are prepared as particles by passing the gel mass through a sieve, and are thus highly elastic and advantageous in maintaining shape and improving volume.

For example, U.S. Pat. No. 8,357,795 describes an injectable monophasic hyaluronic acid filler which is extrudable through a fine gauge needle. U.S. Pat. No. 5,827,937 describes a biphasic hyaluronic acid filler.

Meanwhile, studies have been continued to develop fillers which exhibit ideal in vivo properties as well as ideal surgical usability. However, hyaluronic acid fillers showing excellent in vivo stability have high stiffness and viscosity, and are thus difficult to inject through a fine gauge needle. In contrast, hyaluronic acid fillers which are easily injectable through a fine gauge needle may have a problem of low in vivo stability. Accordingly, there is a need for hyaluronic acid, fillers which are excellent in both viscosity and elasticity.

With this background, the present inventors studied to develop hyaluronic acid fillers having optimal viscoelasticity and surgical usability, and as a result, they have found that two or more hyaluronic acid gels having different phases are mixed by revolution/rotation at a particular speed to prepare a crosslinked hyaluronic acid composition having both monophasic and biphasic characteristics, thereby completing the present invention.

SUMMARY OF THE INVENTION

An object of the present invention is to provide a method of preparing a hyaluronic acid composition for tissue restoration, the method including the step of mixing two or more hyaluronic acid gels by revolution/rotation at a revolution speed of 100 rpm to 400 rpm and a rotation speed of 100 rpm to 400 rpm.

Another object of the present invention is to provide a hyaluronic acid composition with both monophasic and biphasic characteristics for tissue restoration, which is prepared by revolution/rotation of a mixture of two or more hyaluronic acid gels which are different from each other in viscous modulus and elastic modulus.

Still another object of the present invention is to provide a method of restoring a tissue, the method including the step of administering the hyaluronic acid composition with both monophasic and biphasic characteristics for tissue restoration to a subject.

Still another object of the present invention is to provide a quasi-drug composition including the hyaluronic acid composition with both monophasic and biphasic characteristics for tissue restoration.

BRIEF DESCRIPTION OF THE DRAWINGS

FIG. 1a shows monophasic hyaluronic acid prepared according to an exemplary embodiment of the present invention, and FIG. 1b shows biphasic hyaluronic acid prepared according to an exemplary embodiment of the present invent ion;

FIG. 2a is an image of a simple mixture of monophasic hyaluronic acid and biphasic hyaluronic acid, and FIG. 2b is an image of a hyaluronic acid composition with both monophasic and biphasic characteristics, prepared according to an exemplary embodiment of the present invention;

FIG. 3a is an image taken immediately after intradermal injection of hyaluronic acid into a mouse, and FIG. 3b is an image at 10 weeks after intradermal injection of hyaluronic acid into a mouse, in which A represents monophasic hyaluronic acid prepared according to an exemplary embodiment, of the present, invention, B represents biphasic hyaluronic acid prepared according to an exemplary embodiment of the present invention, and C represents a hyaluronic acid composition with both monophasic and biphasic characteristics prepared according to an exemplary embodiment of the present invention (hereinafter, the same as above);

FIG. 4 shows changes in the vertical height of the tissue at 1 day (left) and 10 weeks (right) after intradermal injection of hyaluronic acid into a mouse;

FIG. 5 shows initial swelling and degradation (residual amount) after intradermal injection of hyaluronic acid into a mouse; and FIG. 6 shows a comparison of viscosity between a hyaluronic acid composition with both monophasic and biphasic characteristics according to an exemplary embodiment and biphasic fillers and monophasic fillers.

DETAILED DESCRIPTION OF THE PREFERRED EMBODIMENTS

To achieve the above objects, an aspect provides a method of preparing a hyaluronic acid composition for tissue restoration, the method including the step of mixing two or more hyaluronic acid gels by revolution/rotation.

Another aspect provides a method of preparing a hyaluronic acid composition for tissue restoration, the method including the step of mixing two or more hyaluronic acid gels by revolution/rotation at a revolution speed of 100 rpm to 400 rpm and a rotation speed of 100 rpm to 400 rpm.

The present inventors demonstrated for the first time that when a hyaluronic acid gel having a desired viscous modulus and a hyaluronic acid gel having a desired elastic modulus are subjected to revolution/rotation at a particular revolution speed and a particular rotation speed in order to improve viscoelasticity and surgical usability of the known crosslinked hyaluronic acid composition, a crosslinked hyaluronic acid composition with both monophasic and biphasic characteristics can be prepared.

Hereinafter, the preparation method of the present invention will be described in detail.

The hyaluronic acid is a straight-chain polymer in which β-D-N-acetylglucosamine and β-D-glucuronic acid are alternately linked to each other. In the present, invention, the hyaluronic acid may include all of hyaluronic acid itself, salts thereof, and combinations thereof. The hyaluronic acid may have a molecular weight of 100,000 Da to 5,000,000 Da, but is not limited thereto. The salts of hyaluronic acid may include inorganic salts such as sodium hyaluronate, potassium hyaluronate, calcium hyaluronate, magnesium hyaluronate, zinc hyaluronate, cobalt hyaluronate, etc., and organic salts such as tetrabutylammonium hyaluronate, etc. In the present invention, hyaluronic acid may be used as hyaluronic acid itself or a salt thereof singly, or by combination of two or more of hyaluronic acid itself or a salt thereof. The hyaluronic acid or the salt thereof may be isolated from microorganisms, or synthesized or purchased, but is not limited thereto. For example, the hyaluronic acid may be isolated, and purified from a microorganism belonging to the species Streptococcus (Streptococcus equi, Streptococcus zooepidsmicus).

The hyaluronic acid gel may mean hyaluronic acid having a gel-phase, and it may have the same meanings as hyaluronic acid hydrogei or hydrated gel. For example, the hyaluronic acid gel means covalently crosslinked hyaluronic acids via hydroxyl groups. Water content or crosslinking ratio of hyaluronic acid may be controlled by a general method used, in the art.

The hyaluronic acid gel may be crosslinked by a crosslinking agent. The crosslinking agent may be, but is not limited to, ethylene glycol diglycidyl ether (EGDGE), 1,4-butandiol diglycidyl ether (BDBE), 1,6-hexanediol diglycidyl ether, propylene glycol diglycidyl ether, polypropylene glycol diglycidyl ether, diglycerol polyglycidyl ether, EDC (1-ethyl-3-(3-dimethylaminopropyl) carbodiinside), DVS (divinyl sulfone), BCDI (biscarbodiimide), or a combination thereof.

In the present invention, a mixture of hyaluronic acid gels may be prepared by mixing the hyaluronic acid gels, and the mixing may mean a simple, homogeneous or heterogeneous mixing, blending or stirring of two or more materials by a method generally used in the art.

The mixture of two or more hyaluronic acid gels may mean a mixture of two or more hyaluronic acid gels which are different from each other in terms of viscous modulus and elastic modulus.

As used herein, the term "viscous modulus" represents the extent of viscosity, which is defined as the resistance of a fluid to flow, and it may have the same meaning as viscosity degree or viscosity. Viscous modulus may be expressed as G". As a hyaluronic acid gel has high viscous modulus, its surgical usability increases and it is useful for shaping delicate areas. For example, monophasic hyaluronic acid fillers have high viscous modulus, and are thus easy to inject and suitable for shaping delicate areas.

As used herein, the term "elastic modulus" is defined as the ratio of stress to deformation of an elastic material within the elastic limit. Elastic modulus may be expressed as G'. As a hyaluronic acid gel has high elastic modulus, it is hard and has high resistance to deformation. For example, biphasic hyaluronic acid fillers have high elastic modulus and are thus advantageous in maintaining shape and improving volume.

In the present invention, viscous modulus and elastic modulus of the crosslinked hyaluronic acid composition may be measured using a rheometer, but are not limited thereto. The rheometer is used to determine viscoelastic properties (viscous modulus and elastic modulus) of a sample by placing the sample between parallel plates and measuring the resistance and dissipation to rotation of the oscillating parallel plate.

The mixture of two or more hyaluronic acid gels which are different from each other in terms of viscous modulus and elastic modulus may refer to a mixture of a monophasic hyaluronic acid gel and a biphasic hyaluronic acid gel.

In the present invention, the monophasic hyaluronic acid means hyaluronic acid which mainly exists as a gel, and its physical properties depend on a crosslinking ratio of hyaluronic acid. The monophasic hyaluronic acid is less elastic and more cohesive than the biphasic hyaluronic acid. The term "monophasic" may have the same meaning as single phase. For example, the monophasic hyaluronic acid may have a G' value of less than 300 Pa and a tan δ value of 0.3 or higher at a frequency of 0.01 Hz to 1 Hz.

The tan δ value is a G"/G' value (damping factor), and indicates whether a material behaves like a solid or liquid. When the tan δ value at a frequency of 0.01 Hz to 1 Hz is near 1, the material may be in the liquid state (less elastic) and when the tan δ value at a frequency of 0.01 Hz to 1 Hz is near 0, the material may be defined as an elastic material. Further, it has been reported that as the tan δ value is lower and percentage elasticity (100× G'/(G'+G")) is higher, fillers last longer.

In the present invention, the biphasic hyaluronic acid is a mixed form of particles and a gel of hyaluronic acid, and its physical properties depend on the particle size. The term "biphasic" may have the same meaning as double phase or two-phase. The monophasic hyaluronic acid has high viscosity but low elasticity, and the biphasic hyaluronic acid has high elasticity but low viscosity. For example, the biphasic hyaluronic acid may have a G' value of 300 Pa or more and a tan δ value of less than 0.3 at a frequency of 0.01 Hz to 1 Hz.

According to desired properties (viscosity, elasticity, degree of crosslinking, hardness of gel, degree of tissue restoration, molecular weight, appearance, pH, hyaluronic acid content, etc.) of the hyaluronic acid composition for tissue restoration prepared by the preparation method of the present invention, two or more hyaluronic acid gels having particular characteristics may be selected.

In the present invention, the revolution/rotation step means that revolution and rotation are performed at the same time. For example, the revolution/rotation may mean that the mixture is subjected to revolution/rotation at a revolution speed of 100 rpm to 400 rpm and a rotation speed of 100 rpm to 400 rpm.

For example, the revolution speed may be set to be equal to the rotation speed. For another example, the revolution speed and/or rotation speed may be maintained at a speed (rpm) within the range of 100 rpm to 400 rpm for a predetermined, time, or may be decreased/increased.

If the revolution speed or/and the rotation speed is(are) less than 100 rpm, bubbles are formed in the reaction product to deteriorate the appearance, and viscosity becomes less than 20,000 cP. Therefore, it is difficult to provide a hyaluronic acid composition having both monophasic and biphasic characteristics (Tables 3 and 5). Further, if the revolution speed or/and rotation speed exceed(s) 400 rpm, heat is generated by revolution or/and rotation. At this time, the reaction product is deteriorated because hyaluronic acid has poor heat resistance. Therefore, the product is not suitable for tissue restoration.

As a non-limiting example, the revolution speed may be 100 rpm to 400 rpm, 150 rpm to 300 rpm, or 180 rpm to 230 rpm.

As a non-limiting example, the rotation speed may be 100 rpm to 400 rpm, 150 rpm to 300 rpm, or 180 rpm to 230 rpm.

The revolution/rotation may be performed using a revolution/rotation mixer generally used in the art.

The step may be performed under vacuum conditions. The vacuum conditions may mean a pressure condition of less than 25 Torr. The existing bubbles may be removed and generation of bubbles during mixing may be prevented by performing the revolution/rotation under vacuum conditions, thereby increasing binding of two or more hyaluronic acid gels which are different from each other in terms of viscous modulus and elastic modulus.

The step may be performed for 7 minutes to 30 minutes. In an exemplary embodiment according to the present invention, when the revolution/rotation was performed for less than 7 minutes, generation of bubbles was observed, and thereby physicochemical standards were not met (Table 3).

Further, when revolution/rotation was performed for more than 30 minutes, excessive heat was generated to cause denaturation of hyaluronic acid, resulting in an increase of operating costs.

For example, the step may be performed for 10 minutes to 25 minutes.

The hyaluronic acid composition for tissue restoration which is prepared by the revolution/rotation may have both monophasic and biphasic characteristics. The hyaluronic acid composition prepared in an exemplary embodiment of the present invention was found to have high elastic modulus to show advantages of maintaining the shape and increasing the volume (biphasic characteristic; FIGS. 3a, 3b, and 4), and maintaining the volume for a long time, compared to the biphasic hyaluronic acid, indicating its in vivo stability (monophasic characteristic; FIG. 5). Accordingly, the preparation method of the present invention may be performed to provide the hyaluronic acid composition with both monophasic and biphasic characteristics for tissue restoration.

Further, the hyaluronic acid composition for tissue restoration of the present invention was found to have a viscosity between a viscosity of a monophasic hyaluronic acid composition and a viscosity of a biphasic hyaluronic acid composition, thereby exhibiting both monophasic and biphasic characteristics (FIG. 6).

Further, two or more hyaluronic acid gels having different phases, that is, viscous modulus and elastic modulus, may be mixed with each other by the preparation method of the present invention, thereby homogenously mixing them while meeting physicochemical standards (appearance, pH, viscosity, osmotic pressure, etc. of the composition). Therefore, by selecting hyaluronic acid gels to be mixed, it is possible to provide a hyaluronic acid composition having desired characteristics for tissue restoration.

Meanwhile, the tissue restoration means temporal or semi-permanent improvement or restoration of facial or body wrinkles, or improvement of facial contours, tissue volumization, or tissue regeneration such as scar treatment by injection of the composition. The tissue may be a part of the face or body.

The hyaluronic acid composition for tissue restoration may be filled into a syringe to be injected into the skin layer.

For example, in the preparation method, a mixture of two or more hyaluronic acid gels may include 50 parts by weight to 70 parts by weight of a monophasic hyaluronic acid gel and 50 parts by weight to 30 parts by weight of a biphasic hyaluronic acid gel. For example, the mixture may include 50 parts by weight to 60 parts by weight of a monophasic hyaluronic acid gel and 50 parts by weight to 40 parts by weight of a biphasic hyaluronic acid gel. For example, the mixture may include a monophasic hyaluronic acid gel and a biphasic hyaluronic acid gel at a ratio of 1:0.8 to 1.2 parts by weight (0.6 or more and less than 1.2). When the hyaluronic acid composition for tissue restoration which is prepared by using the mixture according to the present invention is injected into the body, it may maintain tissue restorability for 6 months to 9 months.

For another example, in the preparation method, a mixture of two or more hyaluronic acid gels may include 30 parts by weight to 60 parts by weight of a monophasic hyaluronic acid gel and 70 parts by weight to 40 parts by weight of a biphasic hyaluronic acid gel. For example, the mixture may include 40 parts by weight to 50 parts by weight of a monophasic hyaluronic acid gel and 60 parts by weight to 50 parts by weight of a biphasic hyaluronic acid gel. For example, the mixture may include a monophasic hyaluronic acid gel and a biphasic hyaluronic acid gel at a ratio of 1:1.2 to 2 parts by weight (1.2 or more and less than 2). When the hyaluronic acid composition for tissue restoration which is prepared by using the mixture according to the present, invention is injected into the body, it may maintain tissue restorability for 9 months to 12 months.

For still another example, in the preparation method, a mixture of two or more hyaluronic acid gels may include 20 parts by weight to 50 parts by weight of a monophasic hyaluronic acid gel and 80 parts by weight to 50 parts by weight of a biphasic hyaluronic acid gel. For example, the mixture may include 30 parts by weight to 40 parts by weight of a monophasic hyaluronic acid gel and 70 parts by weight to 60 parts by weight of a biphasic hyaluronic acid gel. For example, the mixture may include a monophasic hyaluronic acid gel and a biphasic hyaluronic acid gel at a ratio of 1:2 to 4 parts by weight (2 or more and less than 4). When the hyaluronic acid composition for tissue restoration which is prepared by using the mixture according to the present invention is injected into the body, it may maintain tissue restorability for 12 months to 15 months.

Therefore, by selecting two or more desired hyaluronic acid gels in the preparation method of the present invention, it is possible to provide a hyaluronic acid composition for tissue restoration having desired characteristics.

Another aspect provides a hyaluronic acid composition with both monophasic and biphasic characteristics for tissue restoration, which is prepared by revolution/rotation of a mixture of two or more hyaluronic acid gels which are different from each other in viscous modulus and elastic modulus.

The composition may be prepared by the above preparation method.

In detail, the composition may be prepared by a preparation method including the step of revolution/rotation of the mixture of two or more hyaluronic acid gels which are different from each other in viscous modulus and elastic modulus, at a revolution speed of 100 rpm to 400 rpm and a rotation speed of 100 rpm to 400 rpm. For example, the mixture of two or more hyaluronic acid gels which are different from each other in viscous modulus and elastic modulus may be a mixture of a monophasic hyaluronic acid gel and a biphasic hyaluronic acid gel. The monophasic, biphasic, tissue restoration, and hyaluronic acid are the same as described above.

The hyaluronic acid composition for tissue restoration may be prepared by homogeneously or heterogeneously mixing two or more hyaluronic acid gels which are different from each other in viscous modulus and elastic modulus.

According to an exemplary embodiment of the present invention, it was confirmed that the hyaluronic acid composition for tissue restoration has physicochemical properties of (a) having no apparent bubbles, and being colorless and transparent; (b) having a pH of 7±1; (c) having a viscosity of 20,000 cP to 50,000 cP; and (d) having an osmotic pressure of 0.325 Osmol/kg±10% on average, meeting requirements for a medical device.

If necessary, the composition may be charged with other general additives such as an antioxidant, a buffer, and/or a bacteriostatic agent, a diluent, a dispersing agent, a surfactant, a binder, a lubricant, a topical anesthetic, etc.

Still another aspect of the present invention provides a method of restoring a tissue, the method including the step of administering the hyaluronic acid composition with both monophasic and biphasic characteristics for tissue restoration to a subject.

The administration means introduction of the composition of the present invention to a subject by any proper method, in particular, via a parenteral route such as injection. Administration frequency of the composition of the present invention may be, but is not limited to, once a day or several times a day in divided doses.

The subject means any animal including humans. The animal may be a human as well as a mammal such as a cow, horse, sheep, pig, goat, camel, antelope, dog, or cat in need of tissue restoration, but is not limited thereto.

Still another aspect of the present invention provides a quasi-drug composition including the hyaluronic acid composition with both monophasic and biphasic characteristics for tissue restoration.

The quasi-drug may be defined as a product with a purpose of tissue restoration of a subject, which is not categorized as a medical device or machine, or the like. For example, it means a product that is used for the purposes of diagnosis, medical care, alleviation, treatment or prevention of disease in human beings or animals, excluding appliances, machinery and equipment, and a product other than an appliance, machinery or equipment that is used for the purpose of exerting pharmacological effects on the structure or functions of human beings or animals.

When the composition according to the present invention is used as a quasi-drug additive, the composition may be properly used as it is, or together with other quasi-drugs or quasi-drug components according to a general method. The amount of the active ingredient to be mixed may be determined depending on the purpose of use.

Hereinafter, the present, invention will be described in more detail with reference to the following Examples. However, these Examples are for illustrative purposes only, and the invention is not intended to be limited by these Examples.

Example 1 to 3 and Preparation Examples 1 to 3

Example 1

Preparation of Monophasic Hyaluronic Acid Gel 10 g of sodium hyaluronate, 81 g of purified water, and 9 g of 1 M NaOH (1 M sodium hydroxide) were stirred under vacuum at 400 rpm until the mixture became a transparent gel without particles. Thereafter, 0.5 g of a crosslinking agent (BDDE, butanediol diglycidyl ether) was added, followed by stirring. After completing the stirring, the container was sealed and the mixture was allowed to undergo crosslinking reaction for 1 hour at 80 rpm and 50° C. Then, the container was left at 27° C. for 16 hours to prepare a gel.

To remove the remaining reagent, the obtained, gel was added to 30 L of 0.9× PBS (phosphate buffered saline) solution, which was replaced with a fresh solution every 3 hours (three times per day for 5 days). Thereafter, this solution was passed through a mortar grinder (RS 200, Retsch) for 40 minutes to prepare a monophasic hyaluronic acid gel.

FIG. 1a is an optical microscope image of the monophasic hyaluronic acid gel.

Example 2

Preparation of Biphasic Hyaluronic Acid Gel 20 g of sodium hyaluronate, 117 g of purified water, and 13 g of 1 M NaOH (1 M sodium hydroxide) were stirred under vacuum at 400 rpm until the mixture became a transparent gel without particles. Thereafter, 1 g of a crosslinking agent (BDDE, butanediol diglycidyl ether) was added, followed by stirring. After completing the stirring, the container was sealed and the mixture was allowed to undergo crosslinking reaction for 1 hour at 80 rpm and 50° C. Then, the container was left at 27° C. for 16 hours to prepare a gel.

To remove the remaining reagent, the obtained gel was added to 30 L of 0.9× PBS (phosphate buffered saline) solution, which was replaced with a fresh solution every 3 hours (three times per day for 5 days). Thereafter, this solution was passed through a standard test sieve of 1000 μm to prepare a biphasic hyaluronic acid gel (FIG. 2a).

FIG. 1b is an optical microscope image of the biphasic hyaluronic acid gel.

Example 3

Preparation of Hyaluronic Acid Composition with Monophasic and Biphasic Characteristics The monophasic hyaluronic acid gel prepared in Example 1 and the biphasic hyaluronic acid gel prepared in Example 2 were mixed at a mixing ratio of the following Table 1, and the mixture (FIG. 2a) was injected to a revolution/rotation paste mixer (Daenwa Tech Co., Ltd.), and then a revolution speed and a rotation speed were set at 200 rpm, respectively. The mixture was subjected to revolution/rotation for 20 minutes under vacuum (3.5 Torr) to prepare a hyaluronic acid composition with monophasic and biphasic characteristics (FIG. 2b).

FIG. 2a is an image of the mixture before revolution/rotation, showing a heterogeneous mixture of a gel and particles. FIG. 2b is an image of the mixture after revolution/rotation, showing a colorless, transparent appearance without debris.

Preparation Example 1 to Preparation Example 3

Packing and Sterilization of Syringe

Each of the resultants prepared in Examples 1, 2, and 3 was packed into a syringe at an equal amount, and sterilized by autoclaving to prepare a formulation containing 20 mg/mL of hyaluronic acid (in the following Preparation Example 1, Preparation Example 2, and Preparation Example 3), respectively.

Experimental Examples 1 to 5

1-1. Test of Volumization

The formulations of Preparation Example 1, Preparation Example 2, and Preparation Example 3 were intradermally injected into a mouse. FIG. 3a is an image after intradermal injection of the formulations of Preparation Examples 1 to 3 into a mouse, and FIG. 3b is an image at 10 weeks after intradermal injection of the formulations of Preparation Examples 1 to 3 into a mouse.

As a result, as shown in FIG. 4, the vertical height of the tissue injected with the formulation of Preparation Example 3 (C of FIG. 4) was found to be higher than those of the monophasic formulation of Preparation Example 1 (A of FIG. 4) and the biphasic formulation of Preparation Example 2 (B of FIG. 4). At 10 weeks after injection, the vertical height of the tissue injected with the formulation of Preparation Example 3 (C of FIG. 4) was also found to be higher than those of the monophasic formulation of Preparation Example 1 (A of FIG. 4) and the biphasic formulation of Preparation Example 2 (B of FIG. 4).

These results suggest that the formulation of Preparation Example 3 has high elastic modulus to exhibit advantages of maintaining the shape and increasing the volume, thereby also having a biphasic characteristic.

1-2. Test of Initial Swelling and Degradation

As a result of intradermal injection of the formulations of Preparation Example 1, Preparation Example 2, and Preparation Example 3 into a mouse, as shown in FIG. 5, the biphasic formulation of Preparation Example 2 (-✱-B) showed a very high degradation rate and thus hardly remained after 5 hours, whereas a residual amount of the formulation of Preparation Example 3 (-▦-C) was large, compared to that of the biphasic formulation of Preparation Example 2 (-✱-B), It is important to increase duration of the injectable volumizing filler.

Further, the formulation of Preparation Example 3 (-▦-C) showed low initial swelling, compared to the monophasic formulation of Preparation Example 1 (-▲-A) and the biphasic formulation of Preparation Example 2 (-✱-B). Therefore, the formulation of Preparation Example 3 reduces a recovery time after injection of the filler.

The formulation of Preparation Example 3 has a high elastic modulus and also offers a long-lasting volume compared to the biphasic formulation, thereby showing in vivo stability, and also shows low initial swelling compared to the monophasic or biphasic formulation, indicating an advantage of having both monophasic and biphasic characteristics.

Experimental Example 2

Test of Safety

A safety test of the hyaluronic acid composition prepared in Example 3 was performed (by Korea Testing & Research Institute (KTR)), and as shown in the following Table 1, it showed lower toxicity, residual amount of solvents, pH, and osmotic pressure than reference values, indicating that the composition has in vivo safety.

TABLE 1

Result of safety test

| Test items | Result value | Reference value |
|---|---|---|
| Endotoxin (LAL Test) | <0.06 EU/mg | ≥0.5 EU/mg |
| Residual BDDE | Not detected | <2 ppm |
| pH | 7 | 7 |
| Osmotic pressure | 0.339 Osmol/kg | 0.325 Osmol/kg |

Experimental Example 3

Results of Physiocochemical Test According to Revolution/Rotation Speed

In Example 3, revolution/rotation was maintained for 5 minutes, 10 minutes, or 20 minutes, respectively and at a speed of 50 rpm, 100 rpm, or 200 rpm, respectively to prepare hyaluronic acid compositions. Appearance, pH of medicinal liquid, viscous modulus, and osmotic pressure of each composition were tested according to the method of Table 2 to examine whether they meet the following criteria.

TABLE 2

| Test items | Test criteria | Test method |
|---|---|---|
| Appearance | No bubbles | Gross observation |
| pH of medicinal liquid | 7 ± 1 | pH measuring method of the general test method of the Korean Pharmacopoeia |
| Viscosity | 20,000 cP to 50,000 cP | viscosity measuring method of the general test method of the Korean Pharmacopoeia |
| Osmotic pressure | 0.325 Osmol/kg ± 10% on average | Osmotic pressure measuring method of the general test method of the Korean Pharmacopoeia |

3-1. Observation of Gross Appearance

Appearance was tested by the method of Table 2, and as a result, appearance was acceptable when revolution/rotation was performed at a speed of 200 rpm for an operating time of 10 minutes and 20 minutes. However, when revolution/rotation was performed at a speed of 100 rpm or lower, or for an operating time of 5 minutes or shorter, bubbles were observed in the composition, indicating that quality of the product is unacceptable.

TABLE 3

| | | Revolution/rotation speed | | |
|---|---|---|---|---|
| Operating time | | 50 rpm | 100 rpm | 200 rpm |
| Time | 5 minutes | Bubbles (unacceptable) | Bubbles (unacceptable) | Bubbles (unacceptable) |
| | 10 minutes | Bubbles (unacceptable) | Bubbles (unacceptable) | No bubbles (acceptable) |
| | 20 minutes | Bubbles (unacceptable) | Bubbles (unacceptable) | No bubbles (acceptable) |

3-2. Measurement of pH of Medicinal Liquid pH was measured by the method of Table 2, and as a result, the revolution/rotation speed and the operating time hardly affect pH values, as shown in the following Table 4.

TABLE 4

| Operating time | Revolution/rotation speed | | |
|---|---|---|---|
| | 50 rpm | 100 rpm | 200 rpm |
| Time 5 minutes | 6.94 (acceptable) | 6.95 (acceptable) | 6.95 (acceptable) |
| 10 minutes | 6.95 (acceptable) | 6.95 (acceptable) | 6.95 (acceptable) |
| 20 minutes | 6.95 (acceptable) | 6.95 (acceptable) | 6.95 (acceptable) |

3-3. Measurement of Viscosity

Viscosity was measured by the method of Table 2, and as a result, the most acceptable viscosity was obtained at a revolution/rotation speed of 200 rpm, as shown in the following Table 5. However, the composition has unacceptable viscosity at a revolution/rotation speed of 100 rpm or lower.

TABLE 5

| Operating time | Revolution/rotation speed | | |
|---|---|---|---|
| | 50 rpm | 100 rpm | 200 rpm |
| Time 5 minutes | 12337.4 cP (unacceptable) | 14405.2 cP (unacceptable) | 33205.6 cP (acceptable) |
| 10 minutes | 12697.6 cP (unacceptable) | 15983.4 cP (unacceptable) | 32932.6 cP (acceptable) |
| 20 minutes | 14539.7 cP (unacceptable) | 15983.4 cP (unacceptable) | 32814.4 cP (acceptable) |

3-4. Measurement of Osmotic Pressure

Osmotic pressure was measured by the method of Table 2, and as a result, the revolution/rotation speed and the operating time hardly affect osmotic pressure, as shown in the following Table 6.

TABLE 6

| Operating time | Revolution/rotation speed | | |
|---|---|---|---|
| | 50 rpm | 100 rpm | 200 rpm |
| Time 5 minutes | 0.313 Osmol/kg (acceptable) | 0.308 Osmol/kg (acceptable) | 0.320 Osmol/kg (acceptable) |
| 10 minutes | 0.315 Osmol/kg (acceptable) | 0.326 Osmol/kg (acceptable) | 0.309 Osmol/kg (acceptable) |
| 20 minutes | 0.316 Osmol/kg (acceptable) | 0.324 Osmol/kg (acceptable) | 0.338 Osmol/kg (acceptable) |

These results indicate that when a mixture of two or more hyaluronic acid gels having different phases is subjected to revolution/rotation at a revolution speed of 150 rpm to 250 rpm and a rotation speed of 150 rpm to 250 rpm, a filler meeting the preparation standards is prepared.

Experimental Example 4

Comparison of Duration According to Mixing Ratios of Example 1 and Example 2

The monophasic hyaluronic acid gel prepared in Example 1 and the biphasic hyaluronic acid gel prepared in Example 2 were mixed at a mixing ratio of the following Table 7, and the mixture was subjected to revolution/rotation under the same conditions as in Preparation Example 3. Thereafter, the product was packed into a syringe, and sterilized by autoclaving to prepare the compositions of Preparation Example 4 to Preparation Example 6.

TABLE 7

| Example 1:Example 2 (wt %) | | |
|---|---|---|
| Preparation Example 4 | Preparation Example 5 | Preparation Example 6 |
| 50:50 | 40:60 | 30:70 |

A clinical test was performed by intradermal injection of the hyaluronic acid compositions of Preparation Example 4 to Preparation Example 6 to the human body, and as a result, the composition of Preparation Example 4 showed a duration of 6 months to 9 months, the composition of Preparation Example 5 showed a duration of 9 months to 12 months, and the composition of Preparation Example 6 showed a duration of 12 months to 15 months.

Therefore, the duration of tissue restorability may be controlled by using the monophasic hyaluronic acid gel and the biphasic hyaluronic acid gel at a desired ratio.

Experimental Example 5

Measurement of Viscosity of Example 3

Viscosity of the hyaluronic acid composition with both monophasic and biphasic characteristics (represented by DN in FIG. 6), which was prepared in Example 3, was measured using a rheometer, and compared with those of commercially available biphasic filler and monophasic filler. The results are shown in FIG. 6 and the following Table 8.

TABLE 8

| Type | | Viscosity (cP) |
|---|---|---|
| Biphasic | R | 13650.27 |
| | RL | 12958.73 |
| | RP | 11665.87 |
| | RPL | 11756.07 |
| | RSQ | 10048.28 |
| | RV | 12585.91 |
| | PD | 11172.77 |
| | PSQ | 9891.93 |
| | IC | 12658.07 |
| Monophasic | JV | 36470.87 |
| | JVL | 34221.88 |
| | JU | 30776.24 |
| | JUP | 31521.89 |
| | JUPxc | 36609.17 |
| Example 3 | DN | 24143.53 |

R: Restylane,
RL: Restylane lidocaine,
RP: Restylane perlane,
RPL: Restylane perlane lidocaine,
RSQ: Restylane subq,
RV: Restylane vital,
PD: Perfecta deep,
PSQ: Perfecta subq,
IC: Yvoire classic,
JV: juvederm voluma,
JVL: juvederm voluma lidocaine,
JU: juvederm ultra,
JUP: juvederm ultra plus,
JUPxc: juvederm ultra plus xc That is, the hyaluronic acid composition for tissue restoration of the present invention has a viscosity between the viscosity of the monophasic hyaluronic acid composition and the viscosity of the biphasic hyaluronic acid composition, indicating that the composition of the present invention has both monophasic and biphasic characteristics.

Based on the above description, it will be understood by those skilled, in the art that the present invention may be implemented in a different specific form without changing the technical spirit or essential characteristics thereof. Therefore, it should be understood that the above embodiment is not limitative, but illustrative in all aspects. The scope of the invention is defined by the appended claims rather than by the description preceding them, and therefore all changes and modifications that fall within metes and bounds of the claims, or equivalents of such metes and bounds are therefore intended to be embraced by the claims.

Effect of the Invention

A hyaluronic acid composition with both monophasic and biphasic characteristics for tissue restoration which is prepared according to a preparation method of the present invention has excellent viscoelasticity and tissue restorability, is long-lasting, and shows low initial swelling to have a fast recovery time, and also has excellent in vivo safety and stability.

What is claimed is:

1. A method of preparing a hyaluronic acid composition for tissue restoration, comprising a step of mixing two or more crosslinked hyaluronic acid gels which are different from each other in terms of viscous modulus and elastic modulus by revolution/rotation at a revolution speed of 150 rpm to 400 rpm and a rotation speed of 150 rpm to 400 rpm, wherein the step is performed for 7 minutes to 30 minutes, wherein the mixture of two or more crosslinked hyaluronic acid gels which are different from each other in terms of viscous modulus and elastic modulus is a mixture of a monophasic crosslinked hyaluronic acid gel and a biphasic crosslinked hyaluronic acid gel.

2. The method of claim 1, wherein the hyaluronic acid composition for tissue restoration has both monophasic and biphasic characteristics.

3. The method of claim 1, wherein the step is performed under vacuum.

4. The method of claim 1, wherein the mixture comprises 50 parts by weight to 70 parts by weight of a monophasic crosslinked hyaluronic acid gel and 50 parts by weight to 30 parts by weight of a biphasic crosslinked hyaluronic acid gel.

5. The method of claim 1, wherein the mixture comprises 30 parts by weight to 60 parts by weight of a monophasic crosslinked hyaluronic acid gel and 70 parts by weight to 40 parts by weight of a biphasic crosslinked hyaluronic acid gel.

6. The method of claim 1, wherein the mixture comprises 20 parts by weight to 50 parts by weight of a monophasic crosslinked hyaluronic acid gel and 80 parts by weight to 50 parts by weight of a biphasic crosslinked hyaluronic acid gel.

7. The method according to claim 1, wherein the revolution speed is from 150 rpm to 300 rpm and the rotation speed is from 150 rpm to 300 rpm.

8. The method according to claim 1, wherein the two or more crosslinked hyaluronic acid gels are BDDE-crosslinked hyaluronic acid gels or DVS-crosslinked hyaluronic acid gels.

9. The method according to claim 8, wherein the two or more crosslinked hyaluronic acid gels are BDDE-crosslinked hyaluronic acid gels.

10. The method of claim 1, wherein the mixture of two or more crosslinked hyaluronic acid gels which are different from each other in terms of viscous modulus and elastic modulus is a mixture of a monophasic BDDE-crosslinked hyaluronic acid gel and a biphasic BDDE-crosslinked hyaluronic acid gel.

11. A hyaluronic acid composition with both monophasic and biphasic characteristics for tissue restoration prepared by the method of claim 1 by revolution/rotation of a mixture of two or more crosslinked hyaluronic acid gels which are different from each other in viscous modulus and elastic modulus.

12. The composition of claim 11, wherein the hyaluronic acid composition for tissue restoration has the following physicochemical properties of:
    (a) having no apparent bubbles, and being colorless and transparent;
    (b) having a pH of 7±1;
    (c) having a viscosity of 20,000 cP to 50,000 cP; and
    (d) having an osmotic pressure of 0.325 Osmol/kg±10% on average.

13. A method of restoring a tissue, the method comprising the step of administering to a subject the hyaluronic acid composition with both monophasic and biphasic characteristics for tissue restoration of claim 11.

14. A quasi-drug composition comprising the hyaluronic acid composition with both monophasic and biphasic characteristics for tissue restoration of claim 11.

* * * * *